United States Patent
Rodenrys

(10) Patent No.: US 8,722,352 B2
(45) Date of Patent: *May 13, 2014

(54) TEST FOR NON-SEPTIC HYPOVOLEMIC SHOCK

(71) Applicant: John Rodenrys, La Jolla, CA (US)

(72) Inventor: John Rodenrys, La Jolla, CA (US)

(73) Assignee: Anazyme, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/686,732

(22) Filed: Nov. 27, 2012

(65) Prior Publication Data

US 2013/0089881 A1    Apr. 11, 2013

Related U.S. Application Data

(62) Division of application No. 12/360,976, filed on Jan. 28, 2009, now Pat. No. 8,338,127.

(60) Provisional application No. 61/024,997, filed on Jan. 31, 2008.

(51) Int. Cl.
  *C12Q 1/37*    (2006.01)

(52) U.S. Cl.
  USPC .......................................................... 435/23

(58) Field of Classification Search
  USPC .......................................................... 435/23
  See application file for complete search history.

(56) References Cited

U.S. PATENT DOCUMENTS

| | | | |
|---|---|---|---|
| 4,275,153 A | 6/1981 | Gargiulo et al. | |
| 5,239,078 A | 8/1993 | Galardy et al. | |
| 6,001,814 A | 12/1999 | Gyorkos et al. | |
| 6,534,283 B1 | 3/2003 | Schmid-Schoenbein et al. | |
| 6,852,697 B1 | 2/2005 | Mathison et al. | |
| 7,113,814 B2 | 9/2006 | Ward et al. | |
| 8,338,127 B2 * | 12/2012 | Rodenrys | 435/23 |
| 2002/0193412 A1 | 12/2002 | Tracey et al. | |
| 2003/0190368 A1 | 10/2003 | Stoughton et al. | |
| 2005/0020580 A1 | 1/2005 | Badley et al. | |
| 2005/0164238 A1 | 7/2005 | Valkirs et al. | |
| 2007/0203448 A1 | 8/2007 | Melker et al. | |
| 2007/0218519 A1 | 9/2007 | Urdea et al. | |
| 2007/0294107 A1 | 12/2007 | Schmid-Schonbein et al. | |

FOREIGN PATENT DOCUMENTS

| | | |
|---|---|---|
| AU | 696945 | 9/1998 |
| CA | 2096225 | 2/1993 |
| EP | 0234095 | 10/1986 |
| WO | 99/46367 | 9/1999 |
| WO | 01/37854 | 5/2001 |
| WO | 2008/103767 | 8/2008 |
| WO | 2009/045543 | 4/2009 |
| WO | 2009/132149 | 10/2009 |
| WO | 2010/087874 | 8/2010 |

OTHER PUBLICATIONS

Altshuler A. et al. Protease Activity Increases in Plasma, Peritoneal Fluid and Vital Organs after Hemorrhagic Shock in Rats. PLoS one 7(3)1-11, Mar. 2012.*

Angeles, O., et al., "Secretory phospholipase A2 (sPLA2). procalcitonin (PCT) and C-reactive protein (CRP) for the diagnosis and differentiation of septic shock and non-septic shock", International Symposium on Intensive Care and Emergency Medicine, Brussels, Belgium, Mar. 21-24, 2000.

Orbe, J. et al., "Independent association of matrix metalloproteinase-10, cardiovascular risk factors and subclinical atherosclerosis", Journal of Thrombosis and Haemostasis, Jan. 2007, vol. 5, No. 1, pp. 91-97.

Penn, A.H., et al., "The intestine as a source of cytotoxic mediators in shock: free fatty acids and degradation of lipid-binding proteins", American Journal of Heart Circulation Physiology, Feb. 8, 2008, vol. 294; pp. H1779-H1792.

* cited by examiner

*Primary Examiner* — Ralph Gitomer

(74) *Attorney, Agent, or Firm* — Fish & Tsang, LLP

(57) ABSTRACT

Methods and kits for diagnosis and staging of non-septic shock are presented in which one or more trypsin protease activities are measured from a biological sample to so identify and/or stage non-septic shock.

4 Claims, 1 Drawing Sheet

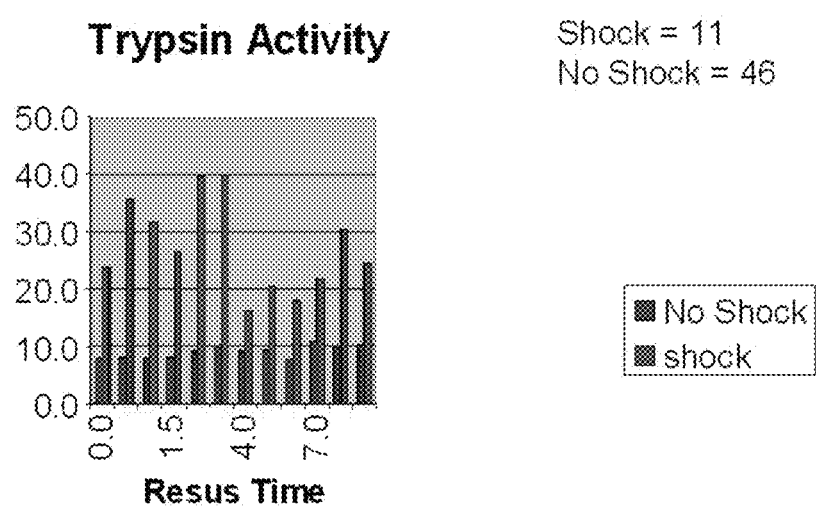

TEST FOR NON-SEPTIC HYPOVOLEMIC SHOCK

This application is a divisional application of U.S. application Ser. No. 12/360,976 filed Jan. 28, 2009 now U.S. Pat. No. 8,338,127, which claims priority to U.S. Provisional Application No. 61/024,997 filed Jan. 31, 2008, incorporated herein by reference in its entirety.

FIELD OF THE INVENTION

The field of the invention is test kits and methods for diagnosis of shock, and especially of non-septic shock.

BACKGROUND

Matrix metalloproteinases (MMPs) and selected other proteases are known to degrade numerous substrates, and especially extracellular matrix proteins. More recently, it was also discovered that some MMPs specifically process certain cell surface receptors to so modify the receptor function, while other MMPs are involved in the generation of apoptotic ligands and chemokine modulation. Not surprisingly, MMPs are therefore involved in various physiological processes, including cell proliferation, migration (adhesion/dispersion), differentiation, angiogenesis, apoptosis and host defense.

Based on the relatively diverse role of MMPs, various diseases have been correlated with MMP activity. For example, increased matrix metalloproteinase-2 (MMP2) transcription has been associated with impaired adipogenesis in type 2 diabetes mellitus (*Biochem Biophys Res Commun.* 2008 Jan. 5), and circulating levels of matrix metalloproteinase (MMP)-10 were reported to be related to inflammation (*J Thromb Haemost.* 2007 January; 5(1):91-7). In other examples, the kallikrein-kinin system was shown to be significantly implicated in numerous conditions, including inflammation, cancer, and in certain pathologies related to cardiovascular, renal and central nervous systems. In still further examples, diabetes was shown to be associated with increased MMP2 expression as disclosed in U.S. Pat. App. No. 2007/218519, and hypertension was associated with altered kallikrenin activities as described in EP00234095A. Consequently, where exacerbated MMP activity is associated with a disease, various forms of treatment of such diseases with MMP inhibitors were proposed as described, for example, in U.S. Pat. App. No. 2007/294107.

Non-septic shock can have various etiologies (hypovolaemic, cardiogenic, distributive, obstructive, endocrine, etc.) and is often diagnosed by overall clinical appearance such as skin tone, blood pressure, heart rate, oxygenation level, mental clarity, etc. However, and especially with compensated non-septic shock, accurate diagnosis is often difficult, and metabolic analysis may assist in the clinical finding. For example, lactic acid may be used as a parameter. More recently, secretory phospholipase A2 (sPLA2), procalcitonin (PCT) and C-reactive protein (CRP) levels were reported as analytical tools for diagnosis and differentiation of septic shock and non-septic shock (Critical Care 2000, 4(Suppl 1):P68). Similarly, diagnosis of septic shock and SIRS has been performed using a multi-marker analysis as described in U.S. Pat. App. No. 2005/164238. However, such analyses are often time consuming, relatively expensive, and can often not be carried out at the point of care (e.g., accident site).

Therefore, while numerous methods of diagnosing shock art (and especially non-septic shock) are known in the art, all or almost all of them suffer from various disadvantages. Thus, there is still a need to provide improved diagnostic tools and methods for identification and staging of non-septic shock.

SUMMARY OF THE INVENTION

According to the present invention, activity of selected proteases in serum or other body fluids are employed to identify and/or stage non-septic shock. Most preferably, the proteases are selected from the group of thrombin, plasmin, trypsin, kallikrein, and selected MMPs. Therefore, especially preferred methods include a step in which protease activity of one or more proteases in a body fluid (e.g., blood or serum) is determined to obtain a test result that is then correlated with a diagnosis or prognosis relative to non-septic shock. In preferred aspects, the determination is performed using one or more substrates from which a fluorescent or otherwise labeled portion is removed.

Therefore, in one aspect of the inventive subject matter, a method of diagnosis of non-septic shock includes a first step in which a sample from a patient is obtained, most typically a blood and/or tissue sample. In another step, activity of at least one protease in the sample is measured to so obtain a test result, which is then correlated with presence and/or progression of non-septic shock in the patient. While not limiting to the inventive subject matter, it is typically preferred that more than one protease activity is measured to obtain an even more sensitive and/or specific result. Particularly contemplated protease activities include those from serine proteases (e.g., thrombin, plasmin, trypsin, kallikrein) and/or matrix metalloproteinases (e.g., collagenases such as MMP1, MMP8, or MMP13, gelatinases such as MMP2 or MMP9, stromelysin-type such as MMP3, MMP10, MMP11, membrane-type such as MMP14, MMP16, or MMP17, and/or matrilysin-type such as MMP7). In further preferred methods, the test results from two or more proteinases are correlated (e.g., via ratio of activities) to obtain additional information on the presence and/or stage of the non-septic shock.

Consequently, the inventor also contemplates a kit for determination and/or staging of non-septic shock that includes one or more proteinase substrates and interpretive information that provides a user with protease activities expected to be within a range considered normal and protease activities considered to be indicative of non-septic shock. Most typically, the proteinase substrate is labeled to facilitate simplified optical detection and quantification, however, non-labeled substrates (e.g., for assays based on mass spectroscopy) are also deemed suitable. Among other suitable substrates, particularly contemplated substrates include those that are specific for thrombin, plasmin, trypsin, kallikrein, and/or a matrix metalloproteinase.

Various objects, features, aspects and advantages of the present invention will become more apparent from the drawing and following detailed description of preferred embodiments of the invention.

BRIEF DESCRIPTION OF THE DRAWING

FIG. 1 is a graph depicting the correlation of no-septic shock and protease activity for an exemplary protease.

DETAILED DESCRIPTION

According to the present invention, non-septic shock is diagnosed, effectiveness of drug treatment for non-septic shock is monitored, and/or prognosis for a patient suffering from non-septic shock is provided by measuring a protease activity of selected proteases in serum or other body fluid and correlating the test result with a diagnostic finding, treatment efficacy, and/or prognosis. Most preferably, activity and/or quantity of at least two proteases are measured in serum, and it is particularly preferred that the proteases are selected from the group of serine proteases and metalloproteinases. Alternatively, or additionally, further diagnostic markers may be used in correlation or without correlation to measured protease activity.

In one especially preferred aspect of the inventive subject matter, blood is drawn from a mammal (typically human or vertebrate) and the cellular fraction is removed to obtain the plasma or serum fraction (typically via centrifugation). Protease activity is then measured by aliquoting small samples to a multiwell plate or other carrier together with appropriately labeled substrates that are most preferably specific for the selected protease. In particularly preferred aspects, the protease activity is determined for at least one, and most typically at least two of thrombin, plasmin, trypsin, kallikrein, and selected MMPs (e.g., collagenases, gelatinases, stromelysin-type, and/or membrane-type). The so obtained test result is then compared to corresponding test results from healthy donors, and the particular activity profile is then associated with a diagnostic finding, treatment efficacy, and/or prognosis.

FIG. 1 illustrates an exemplary test result from an experiment in which serum trypsin activity in porcine was measured using serum from pigs; one group (shock) was subjected to hypovolumetric shock and the other group (no shock) was not subjected to hypovolumetric shock. As can be clearly seen, trypsin activity was significantly and consistently higher in animals suffering from non-septic shock, typically at a 2-3 fold higher rate. In this graph, resuscitation time is in hours and trypsin activity is in units/ml.

While it is generally preferred that protease activity is measured from at least two distinct proteases in the same serum at substantially the same time, it should be appreciated that only one protease activity may be measured. However, in most preferred aspects, at least two, three, four, and even more protease activities may be measured. Typically, multiple measurements will be performed serially or in parallel in single test device. Thus the activity determinations may be separated in a spatial, spectroscopic, or temporal fashion. Where appropriate, deconvolution may be needed to provide individual results. Alternatively, combined results may also be indicative. Moreover, and especially where multiple data points for a single enzyme are measured, kinetic data (e.g., slope of activity over time) may also be used in generation of test results. Therefore, the test results may be in the form of numeric output (e.g., single test value), graphic output (e.g., linear or sigmoidal graph), calculated output (e.g., slope of graph), or ratio of any of the above for multiple measurements.

Protease tests will typically be based on currently known methods and materials, and it is especially preferred that such tests will include labeled substrates with high specificity to the respective protease. Therefore, suitable thrombin substrates include various commercially available AMC-labeled synthetic peptides (e.g., Technothrombin TGA Fluorogenic substrate [Z-G-G-R-AMC], commercially available from DiaPharma). Similarly, contemplated trypsin substrates include labeled aromatic amides of N-alpha-protected arginine that produce an aromatic amine upon hydrolysis (e.g., BAPNA releases p-nitroaniline, and BANA releases 2-amino-naphthalene that is detected by diazotization and coupling with N-(1-naphthyl)-ethylenediamine to form an azo-dye). Further alternative trypsin substrates include those of U.S. Pat. No. 6,770,764.

Suitable kallikrein substrates include Chromogenix-S2302 (H-D-Prolyl-L-phenylalanyl-Larginine-p-nitroaniline dihydrochloride commercially available from DiaPharma), and plasmin substrates include Chromogenix-S2403 (L-Pyro-glutamyl-L-Phenylalanyl-L-Lysine-p-Nitroaniline hydrochloride).

Likewise, there are numerous MMP substrates known in the art and all of the known substrates are deemed suitable for use herein. For example, contemplated MMP-2 substrates are synthetic peptides as described by (Murphy, G., et al. 1994. J. Biol. Chem. 269, 6632). Other MMP substrates can be obtained from various commercial sources, including Anaspec (San Jose, Calif. 95131), and Biomol International (Plymouth Meeting, Pa. 19462)

Consequently, it should be appreciated that the label in the protease substrate may vary and the particular label will depend at least to some degree on the specific protease and desired assay condition. Analytic methods for protease activity will therefore include fluorescence, luminescence, UV/VIS absorption, radiometric methods, etc. Alternatively, non-labeled substrates may be also used and detection is then preferably performed using separation methods and most preferably using various forms of mass spectroscopy (e.g., MALDI-TOF, ES-MS, etc.) and/or chromatographic methods (e.g., HPLC, FPLC, etc).

In yet further contemplated aspects, protease activity may also be indirectly measured using genetic methods, and particularly genetic array technologies that allow for quantification of expression levels. For example, expression levels may be monitored using rtPCR of mRNA or hnRNA, most typically with whole blood as source material.

Regardless of the manner of obtaining protease activities, it should be appreciated that the results may be individually used, or may be used to form a combined protease activity index, and/or may be used to determine a ratio of one or more first protease activities against one or more distinct second protease activities. Such ratios may be specific for a stage in shock, for progression, and/or indicative of treatment success or failure. Most typically, and compared against a control value from a healthy individual, higher or increasing protease activities will generally be indicative of presence of deepening non-septic shock while lower or declining protease activities will generally be indicative of absence of non-septic shock or effective treatment.

Therefore, it should be recognized that contemplated test results for protease activity may be used as diagnostic tool to confirm or indicate the diagnosis of non-septic shock. For example, where the measured protease activities or activity profiles are above a threshold level considered normal for a healthy person, diagnosis of non-septic shock may be confirmed. Similarly, and especially where multiple measurements of protease activity are made over time, decline or incline in activity or change in ratio may be correlated with treatment success, progression of non-septic shock (e.g., compensated to decompensated). Likewise, measurements may be correlated with expected mortality or other prognosis.

In still further contemplated aspects, the determination of protease activities need not be limited to those from whole blood or serum/plasma, but may also be based on measurements in other body fluids or even biopsy specimen. For example, suitable alternative body fluids include urine, spinal fluid, tear fluid, saliva, etc., and contemplated tissues from which protease activity is measures include skeletal muscle tissue, adipose tissue, and neural tissue.

In still further contemplated aspects, cellular components other than proteases may also be measured, and particularly contemplated components include enzymes, structural proteins, cytokines, and messenger substances. Such cellular components may therefore replace one or more proteases, or may be sued in addition to the protease. For example, where the cellular component is an enzyme, suitable enzymes will especially include various hydrolases (e.g., phosphatases, lipases, etc), kinases (and especially those involved in cell signal transduction such as G-protein coupled kinases, tyrosine kinases, etc.), and enzymes associated with energy metabolism and particularly anaerobic energy metabolism. Contemplated structural proteins will especially include collagens and fragments thereof, while contemplated cytokines will include pro-inflammatory cytokines. Particularly contemplated messenger substances will include chemokines and hormones.

Further cellular non-protease components that have been identified as markers of non-septic shock and include fatty acid binding protein (and all isoforms or family members, including FABP1-FABP11, and FABP5-like 1-7), and various members of the mucin protein family (MUC1 through MUC20). In still further unexpected results, the inventor found increased concentration of hemoglobin in the samples. Therefore, myoglobin may also serve as a potential marker. Additionally observed cellular non-protease components include neuropeptide Y (NPY), and numerous fragments of cleaved cellular receptors (and especially insulin receptor alpha, CD18 receptor, leptin receptors, VEGF receptors).

Moreover, the following non-protease components have been identified as markers of non-septic shock and include several degradation products from the intestine (e.g. mucins as noted above, or intestine specific free fatty acid protein), several degradation products from the pancreas (including digestive enzymes themselves after degradation), various lipid fragments (e.g., FFA), numerous plasma protein degradation fragments, and endothelial fragments derived from the endothelial membrane (e.g., extracellular domains of insulin receptor fragments, VGFR2 fragments, glycocalyx protein fragments, etc.).

Additionally, it was discovered that further systemically observable markers could be indicative of non-septic shock, and among those are olfactorically perceptible markers, most likely due to emission of volatile organic compounds (possibly sulfurous, and especially hydrogen sulfide, or amine-based) that produced a characteristic odor. Moreover, in at least in vivo systems of hypovolaemic shock, discoloration (most typically redness due to increased hemoglobin) of digits and nails was observed.

Consequently, contemplated kits for diagnosis of non-septic shock will include one, and more preferably two or more protease substrates (most preferably labeled) and an instruction to measure protease activity in a patient sample to ascertain or monitor non-septic shock. Most typically, such kit will also include interpretive information that provides a user with protease activities expected to be within a range considered normal, and protease activities considered to be indicative of non-septic shock. Where suitable, such information may also provide further information on ratios of protease activities and associated conditions therewith.

Thus, specific embodiments and applications of proteases in the diagnosis of non-septic shock have been disclosed. It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of testing a mammal for presence, progression or stage of non-septic hypovolemic shock, comprising:
    obtaining a blood sample from the mammal and removing a cellular fraction from the blood to so obtain a serum or plasma fraction;
    adding a substrate for trypsin to the serum or plasma fraction, and measuring a product formed from the substrate to thereby measure activity of the trypsin to obtain a test result; and
    using the test result, upon diagnosis of the mammal as having a shock condition, to ascertain at least one of presence, progression, and stage of non-septic hypovolemic shock in the mammal;
    wherein the step of using the test result comprises a step of correlating the test result with a corresponding test result of a healthy mammal, wherein an increased activity of the trypsin as compared to the healthy mammal is indicative of the at least one of the presence, progression, and stage of non-septic hypovolemic shock.

2. The method of claim 1 further comprising a step of measuring activity of an additional protease.

3. The method of claim 2 wherein the additional protease is selected from the group consisting of thrombin, plasmin, kallikrein, and chymotrypsin.

4. A method of testing a mammal for presence, progression or stage of non-septic hypovolemic shock, comprising:
    obtaining a blood sample from the mammal and removing a cellular fraction from the blood to so obtain a serum or plasma fraction;
    measuring a degradation product from a trypsin protease reaction in the serum or plasma fraction to obtain a test result;
    using the test result, upon diagnosis of the mammal as having a shock condition, to ascertain at least one of presence, progression, and stage of non-septic hypovolemic shock in the mammal;
    wherein the step of using the test result comprises a step of correlation with a corresponding test result of a healthy mammal, wherein an increased presence of the degradation product as compared to the healthy mammal is indicative of the at least one of the presence, progression, and stage of non-septic hypovolemic shock.

* * * * *